United States Patent [19]

Miyake et al.

[11] Patent Number: 5,369,104
[45] Date of Patent: Nov. 29, 1994

[54] PYRIDAZINE COMPOUNDS, THEIR PRODUCTION AND USE

[75] Inventors: Akio Miyake, Hirakata; Yasuhiko Kawano, Suita; Yasuko Ashida, Takatsuki, all of Japan

[73] Assignee: Takeda Chemical Industries, Ltd., Japan

[21] Appl. No.: 997,538

[22] Filed: Dec. 28, 1992

[30] Foreign Application Priority Data

Dec. 27, 1991 [JP] Japan ................... 3-347196
Aug. 19, 1992 [JP] Japan ................... 4-220137

[51] Int. Cl.$^5$ ............... A61K 31/50; A61K 31/55; C07D 487/04; C07D 487/14
[52] U.S. Cl. ............... 514/212; 514/232.5; 514/234.2; 514/248; 540/599; 544/115; 544/116; 544/117; 544/234; 544/236; 558/15; 558/452; 560/150; 564/95; 564/96
[58] Field of Search ............ 544/236, 115, 116, 117; 540/599; 514/248, 212, 232.5, 234.2

[56] References Cited

U.S. PATENT DOCUMENTS

| | | | |
|---|---|---|---|
| 5,145,850 | 9/1992 | Miyake et al. | 514/248 |
| 5,155,108 | 10/1992 | Miyake et al. | 514/248 |
| 5,202,324 | 4/1993 | Miyake et al. | 514/248 |

FOREIGN PATENT DOCUMENTS

| | | |
|---|---|---|
| 381132 | 8/1990 | European Pat. Off. . |
| 440119 | 8/1991 | European Pat. Off. . |
| 444549 | 9/1991 | European Pat. Off. . |

*Primary Examiner*—Emily Bernhardt
*Attorney, Agent, or Firm*—Wegner, Cantor, Mueller & Player

[57] ABSTRACT

Novel compound represented by the formula:

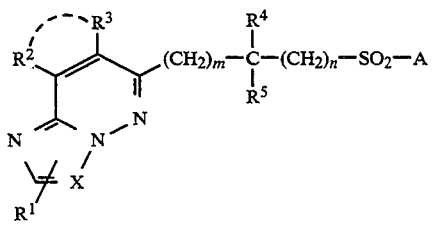

wherein X stands for a methine (i.e. the group —CH=) group or a nitrogen atom; $R^1$ stands for a hydrogen atom, an optionally substituted lower alkyl group or a halogen atom; $R^2$ and $R^3$ respectively stand for a hydrogen atom or an optionally substituted lower alkyl group, or, taken together, may form a 5- to 7-membered ring combined with the adjacent —C=C—; $R^4$ and $R^5$ respectively stands for a hydrogen atom or an optionally substituted lower alkyl group or, taken together, form a 3- to 7-membered homo- or heterocyclic ring combined with the adjacent carbon atom; A stands for an optionally substituted amino group; m and n denote 1 to 4, respectively, or salts thereof which has an antiallergic, antiinflammatory and anti-PAF activity and is useful as an antiasthmatic agent.

29 Claims, No Drawings

PYRIDAZINE COMPOUNDS, THEIR PRODUCTION AND USE

This invention relates to novel imidazopyridazine and triazolopyridazine derivatives or salts thereof, their production and use.

The imidazopyridazine and triazolopyridazine derivatives or their salts of this invention have antiallergic, antiinflammatory, and anti-PAF (platelet activating factor) actions and are useful as an antiasthmatic agent to suppress bronchismus or bronchoconstriction.

In EP-185 346 A2, there are disclosed imidazo[1,2-b]pyridazine compounds of the formula:

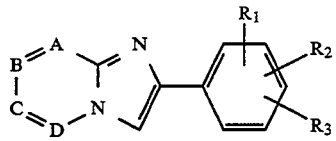

wherein one or two groups of A, B, C and D are a nitrogen atom, and one of them is a hydroxymethine group. The other groups of A, B, C and D are methine, one of which, if next to an nitrogen atom, can be substituted by a hydroxymethine group or an alkylmercapto group; $R_1$ and $R_2$ together complete a phenyl ring which may be substituted by an alkoxy group; $R^3$ stands for a hydrogen atom or an alkoxy group, or one of $R_1$, $R_2$ and $R_3$ are a hydroxy, a phenyl, an alkoxy, an alkylmercapto, an alkylsulphinyl, an amino, an alkylsulphonyloxy, a sulphamoyl, an alkylaminosulphonyl, a dialkylaminosulphonyl, an alkylsulphonamido, a N-alkyl-alkylsulphonamido, a cyano, an aminocarbonyl, an alkylaminocarbonyl or a dialkylaminocarbonyl group; or if $R_2$ and $R_3$ are not both hydrogen atom, or when A, B, C and D, together with imidazole ring, do not complete an imidazo[1,2-b]pyridazine-6(5H)-one, an imidazo[1,2-c]pyrimidine-5(6H)-one or a 5-alkylmercapto-imidazo[1,2-c]pyrimidine-7(8H)-one, one of $R_1$, $R_2$ or $R_3$ can also be an alkoxy or an alkylsulphonyl group; the second of $R_1$, $R_2$ and $R_3$ are a hydrogen atom, a hydroxy or an alkoxy group, the third is a hydrogen atom or an alkoxy group; all alkyl residues contain one or two carbon atoms, their imidazole derivatives, their tautomers or acid addition salts which are useful an antithrombotic and cardiovascular agents shown an antithrombosis action and an action on cardiac blood system, especially a cardio-tonic action.

And, in EP-381 132 A1, it is disclosed that imidazo[1,2-b]pyridazine compounds represented by the following general formula or a salt thereof have an antiallergic, antiinflammatory and anti-PAF actions and are useful as an antiasthmatic agent.

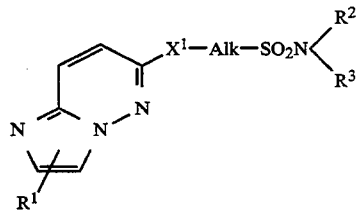

wherein $R^1$ is a hydrogen or a halogen atom, or a lower alkyl group optionally having substituent(s), $R^2$ and $R^3$ are, independently, a hydrogen atom, a lower alkyl group optionally having substituent(s), a cycloalkyl group or a phenyl group optionally having substituent(s) or $R^2$ and $R^3$ together with the adjacent nitrogen atom to which they bond may form a heterocyclic ring optionally having substituent(s), X is an oxygen atom or $S(O)_n$ (n=0 to 2), Alk is a straight or branched chain alkylene group containing 1–10 carbon atoms and optionally having substituent(s).

Further, EP-440 119 A1 discloses imidazo[1,2-b]pyridazine compounds of the formula:

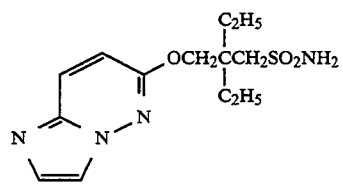

or their salts which are useful as antiasthmatic agent, and EP-444 549 A1 discloses imidazo[1,2-b]pyridazine compounds of the formula:

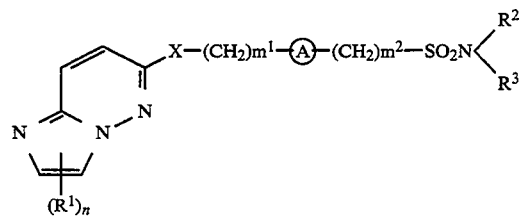

wherein $R^1$ is a halogen atom or a lower alkyl group optionally having substituent(s), $R^2$ and $R^3$ are, independently, a hydrogen atom, a lower alkyl group optionally having substituent(s), a cycloalkyl group or a phenyl group optionally having substituent(s) or $R^2$ and $R^3$ together with the adjacent nitrogen atom to which they bond may form a heterocyclic ring optionally having substituent(s), X is an oxygen atom or $S(O)_k$ (k is zero to two), a group

is a bivalent three to seven membered homocyclic or heterocyclic group optionally having substituent(s), $m^1$ and $m^2$ each is an integer of 0 to 4 and n is an integer of 0 or 1; or its salt, which are useful as antiasthmatics.

The present inventors conducted diligent study on condensed pyridazine compounds and, as a result, they succeeded in synthesizing novel condensed pyridazine compounds which are completely different from the above-mentioned known compounds in the chemical structure, i.e., the side chain is bonded to the imidazo[1,2-b]pyridazine ring through a carbon atom, not through a hetero-atom, and they found that the compounds thus synthesized show, unexpectedly, excellent antiallergic, antiinflammatory, anti-PAF actions and excellent sustained stability, and that they are capable of suppressing bronchismus and bronchoconstriction and are useful as an effective antiasthmatic agent. Based on these findings, the present invention has been accomplished.

The present invention relates to (1) a compound represented by the formula:

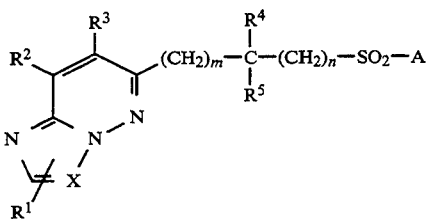

wherein X stands for a methine group or a nitrogen atom; $R^1$ stands for a hydrogen atom, an optionally substituted lower alkyl group or a halogen atom; $R^2$ and $R^3$ respectively stand for a hydrogen atom or an optionally substituted lower alkyl group, or, taken together, may form a 5- to 7-membered ring combined with the adjacent —C=C—; $R^4$ and $R^5$ respectively stand for a hydrogen atom or an optionally substituted lower alkyl group or, taken together, form a 3- to 7-membered homo- or hetero-cyclic ring combined with the adjacent carbon atom; A stands for an optionally substituted amino group; m and n denote a whole number of 1 to 4, respectively] or a salt thereof, (2) a method of producing a compound described in (1) above in (1), which comprises (i) reacting a compound represented by the formula:

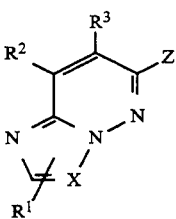

or a salt thereof with a compound represented by the formula:

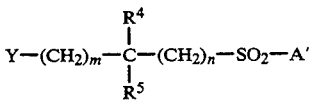

wherein Y and Z stand for groups which are capable of leaving by reacting with each other; A' stands for an optionally protected amino group; and the other symbols are of the same meaning as defined above in (1), or a salt thereof, or (ii) reacting a compound represented by the formula:

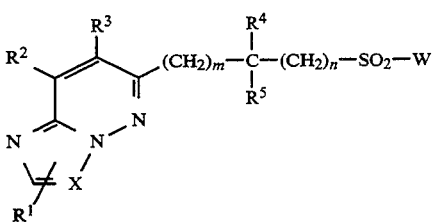

wherein W stands for a halogen atom, and the other symbols are of the same meaning as defined above in (1), or a salt thereof with a compound represented by the formula:

H—A   [V]

wherein A is of the same meaning as defined above in (1), or a salt thereof, and (3) an anti-asthmatic agent, which contains a compound described above in (1).

In the case where the compounds [I] or salts thereof contain asymmetric carbons in the structure, the optically active compounds and a mixture of their racemic modifications are included in the scope of this invention.

The term "lower alkyl" used in this specification means, for example, a straight-chain or branched $C_{1-6}$ alkyl group. As the $C_{1-6}$ alkyl group, use is made of, for example, methyl, ethyl, n-propyl, i-propyl, n-butyl, i-butyl, tert-butyl, n-pentyl and n-hexyl.

The substituents which the "lower alkyl" may optionally include, one to four of those selected from, for example, a hydroxy, an amino, a carboxy, a nitro, a mono- or a di-lower alkylamino (e.g. mono- or di-$C_{1-6}$ alkyl amino including methylamino, ethylamino, propylamino, dimethylamino and diethylamino), a lower alkoxy (e.g. $C_{1-6}$ alkoxy including methoxy, ethoxy, propoxy and hexyloxy), a lower alkylcarbonyloxy (e.g. $C_{1-6}$ alkyl-carbonyloxy including acetoxy and ethylcarbonyloxy) and a halogen atom (e.g. fluorine, chlorine, bromine and iodine).

"A 5- to 7-membered ring formed in combination with the adjacent —C=C—" taken together with $R^2$ and $R^3$ means, for example, a 5- to 7-membered ring consisting of 5 to 7 carbon atoms or carbon atoms and one to four hetero atoms selected from, for example, nitrogen atom, oxygen atom and sulfur atom. More specifically stating, use is often made of, especially, a 5- to 7-membered hydrocarbon ring such as $C_{5-7}$ cycloalkene (e.g. cyclopentene, cyclohexene, cycloheptene or benzene), and a 5- to 7-membered nitrogen-containing heterocyclic ring consisting of carbon atom and nitrogen atom, such as pyrrole, pyridine and piperidine.

"A 3- to 7-membered homocyclic ring formed in combination with the adjacent carbon atom" taken together with $R^4$ and $R^5$ means, for example, a 3- to 7-membered homocyclic ring consisting of carbon atoms. More specifically, use is often made of a $C_{3-7}$ cycloalkane such as cyclopropane, cyclobutane, cyclopentane, cyclohexane or cycloheptane, a $C_{3-7}$ cycloalkene such as cyclopropene, cyclobutene, cyclopentene, cyclohexene or cycloheptene, and benzene. Accordingly, examples of 3- to 7-membered homocyclic groups shown by the formula:

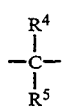

include those shown by formula:

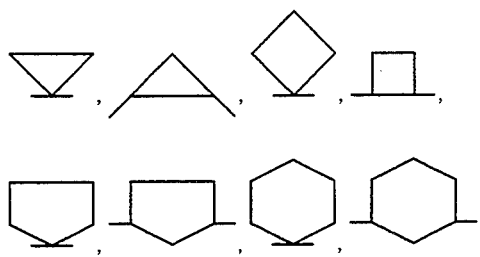

-continued

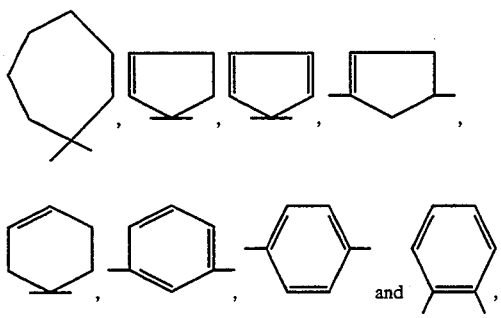

especially those shown by the formula:

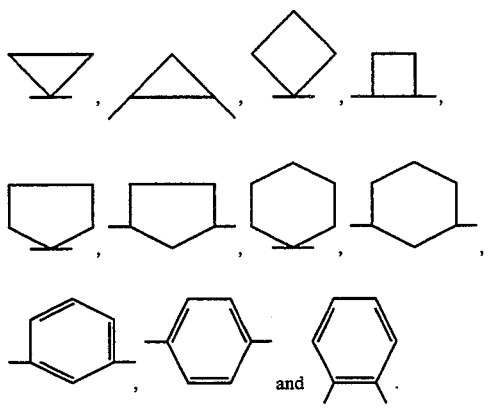

"A 3- to 7-membered heterocyclic ring formed in combination with the adjacent carbon atom" taken together with $R^4$ and $R^5$ means, for example, a 3- to 7-membered heterocyclic ring containing one to four hetero-atoms other than carbon, for example, nitrogen, oxygen and sulfur. More specifically, use is made of, for example, oxetane, tetrahydrofuran, tetrahydropyran, pyrrole, azetidine, pyrrolidine, piperidine, piperazine, tetrahydrothiophene, homopiperidine, morpholine, furan and pyridine. Accordingly, as 3- to 7-membered heterocyclic groups shown by the formula:

use is made, for example, of those shown by the formula

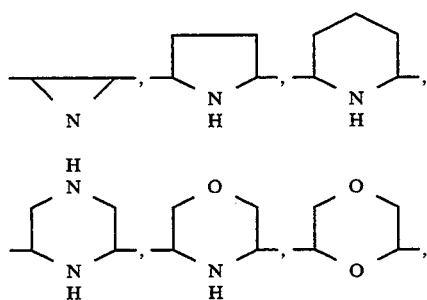

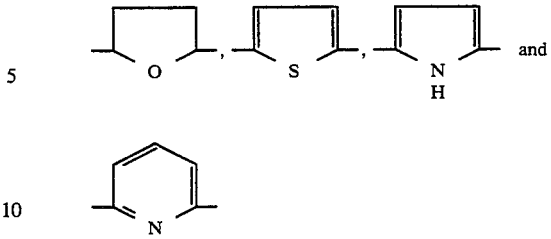

"A 3- to 7-membered homocyclic ring formed in combination with the adjacent carbon atom" and "a 3- to 7-membered heterocyclic ring formed in combination with the adjacent carbon atom" shown by $R^4$ and $R^5$ may optionally be substituted. As such substituents, use is made of one to five of those selected from, for example, optionally substituted lower alkyl, optionally substituted amino, hydroxy, carboxy, nitro, lower alkoxy (e.g. $C_{1-6}$ alkoxy such as methoxy, ethoxy and propoxy) and halogen atoms (e.g. fluorine, chlorine, bromine and iodine). As substituents which the lower alkyl (e.g. such "lower alkyl" as mentioned above) may optionally have, use is made of one to four of those selected from, for example, hydroxyl, amino, mono- or di-lower alkylamino (e.g. mono- or di- $C_{1-6}$ alkylamino such as methylamino, ethylamino, propylamino, dimethylamino or diethylamino), lower alkoxy (e.g. $C_{1-6}$ alkoxy such as methoxy, ethoxy, propoxy or hexyloxy), lower alkylcarbonyloxy (e.g. $C_{1-6}$ alkylcarbonyloxy such as acetyl or ethylcarbonyloxy) and halogen atom (e.g. fluorine, chlorine, bromine and iodine). As substituents which the amino group may optionally have, use is made of one to two of those selected from, for example, $C_{1-6}$ alkyl (e.g. methyl, ethyl or propyl), acyl (e.g. $C_{1-6}$ acyl such as formyl, acetyl, propionyl or butylyl) and 5- to 7-membered cyclic amino (e.g. pyrrolidino, morpholino, piperidino or piperadino).

The term "optionally substituted amino groups" for A mean those represented by the formula:

       [IV]

wherein $R^6$ and $R^7$ respectively stand for a hydrogen atom, an optionally substituted lower alkyl group, an optionally substituted cycloalkyl group or an optionally substituted aryl group or an optionally substituted nitrogen-containing heterocyclic group formed, taken together, in combination with the adjacent nitrogen atom.

The term "cycloalkyl group" means, for example, a $C_{3-6}$ cycloalkyl group. As $C_{3-6}$ cycloalkyl groups, use is made of, for example, cyclopropyl, cyclobutyl, cyclopentyl and cyclohexyl.

The term "aryl group" means, for example, a $C_{6-14}$ aryl group. As $C_{6-14}$ aryl groups, use is made of, for example, phenyl and naphthyl.

As substituents which the "cycloalkyl group" may optionally have, use is made of those similar to "substituents which the lower alkyl group may optionally have" as mentioned above. The number of the substituents is preferably one to four.

As substituents which the "aryl group" may optionally have, use is made of one to five of those selected from, for example, optionally substituted lower alkyl, optionally substituted amino, acetamido, hydroxy, carboxy, nitro, lower alkoxy (e.g. $C_{1-6}$ alkoxy such as methoxy, ethoxy and propoxy), lower alkylcarbonyloxy (e.g. $C_{1-6}$ alkylcarbonyloxy such as acetoxy and ethylcarbonyloxy) and halogen atom (e.g. fluorine, chlorine, bromine and iodine). As substituents which the lower alkyl (e.g. such "lower alkyl" as mentioned above) may have, use is made of one to four of those selected from, for example, hydroxy, amino, mono- or di-lower alkylamino (e.g. mono- or di-$C_{1-6}$ alkylamino such as methylamino, ethylamino, propylamino, dimethylamino and diethylamino), lower alkoxy (e.g. $C_{1-6}$ alkoxy such as methoxy, ethoxy, propoxy and hexyloxy) and halogen atoms (e.g. fluorine, chlorine, bromine and iodine). As substituents which the amino group may optionally have, use is made of one or two of those selected from, for example, $C_{1-6}$ alkyl (e.g. methyl, ethyl and propyl) and 5- or 7-membered cyclic amino (e.g. pyrrolidino, morpholino, piperidino and piperazino).

The term "halogen atom" means, for example, fluorine, chlorine, bromine and iodine.

"The nitrogen-containing heterocyclic group" formed by $R^6$ and $R^7$ in combination with the adjacent nitrogen atom means a group formed by removing one hydrogen atom on a nitrogen atom in the ring of, for example, 3- to 13-membered N-containing heterocyclic ring which contains one nitrogen atom other than carbon atoms and further optionally contains one to three hetero-atoms selected from nitrogen atom, oxygen atom and sulfur atom. More specifically, use is often made of 3- to 9- membered nitrogen-containing heterocyclic groups, for example:

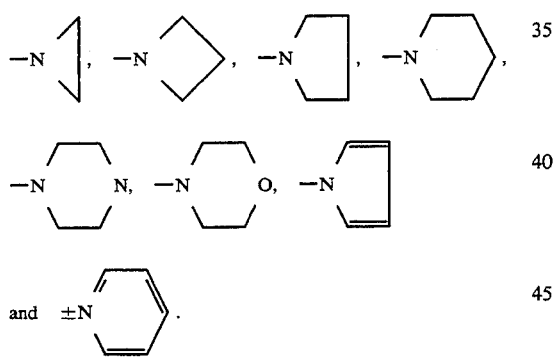

As substituents for the "nitrogen-containing heterocyclic group", use is made of those similar to the substituents which the above-mentioned "3- to 7-membered homocyclic ring formed in combination with the adjacent carbon atom" and "3- to 7-membered heterocyclic ring formed in combination with the adjacent carbon atom" for $R^4$ and $R^5$ may have. The number of the substituents is preferably one to four.

In the above formula, $R^1$ stands for a hydrogen atom, an optionally substituted lower alkyl group or a halogen atom. Preferable examples of $R^1$ include a hydrogen atom or a $C_{1-3}$ alkyl (e.g. methyl, ethyl and n-propyl), and use is often made of, especially, a hydrogen atom.

$R^2$ and $R^3$ respectively stand for a hydrogen atom or an optionally substituted lower alkyl group, and taken together, they may form a 5- to 7-membered ring in combination with the adjacent —C=C—. Preferable examples of $R^2$ and $R^3$ include a hydrogen atom and a $C_{1-3}$ alkyl (e.g. methyl, ethyl and n-propyl). Especially, a hydrogen atom is often used. And, the case where $R^2$ and $R^3$, taken together, form a 5- to 7-membered homocyclic ring in combination with the adjacent —C=C—, is also preferable. Especially, the case where desirable is a $C_{5-8}$ cycloalkene such as cyclohexene or benzene is formed.

$R^4$ and $R^5$ respectively stand for a hydrogen atom or an optionally substituted lower alkyl group, or, taken together, may form a 3- to 7-membered ring combined with the adjacent carbon atom. Preferable examples of $R^4$ and $R^5$ include a hydrogen atom or an optionally substituted $C_{1-3}$ alkyl group. As the "$C_{1-3}$ alkyl group" of the "optionally substituted $C_{1-3}$ alkyl group" shown by $R^4$ and $R^5$, use is made of methyl, ethyl, n-propyl and i-propyl. And, as "substituents", use is made of those similar to the substituents which the term "lower alkyl group" shown by $R^4$ and $R^5$ may have. Especially, use is often made of such cases where $R^4$ and $R^5$ stand for a hydrogen atom or a $C_{1-3}$ alkyl (e.g. methyl, ethyl and n-propyl).

Also in the case where $R^4$ and $R^5$, taken together, form a 3- to 7-membered homo- or heterocyclic ring in combination with the adjacent carbon atom, preferable examples of groups represented by the formula:

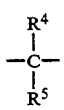

include those shown by the formula:

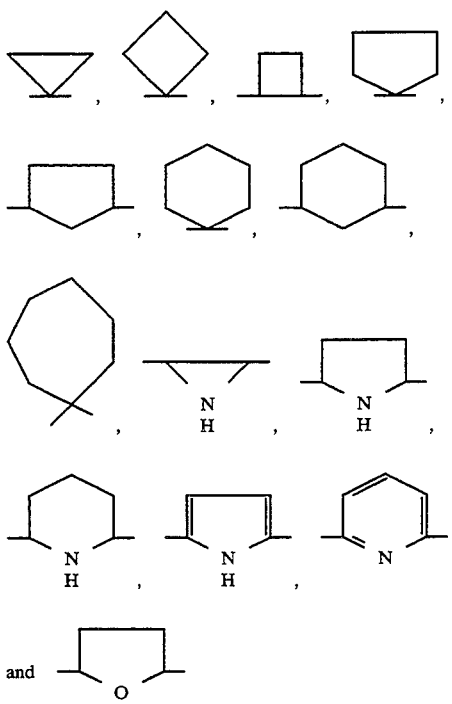

and especially those shown by the formula:

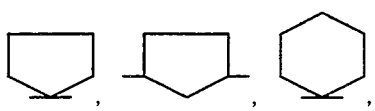

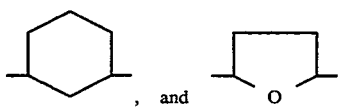

Preferable examples of $R^6$ and $R^7$ include a hydrogen atom, a $C_{1-6}$ alkyl group (e.g. methyl, ethyl, n-propyl, i-propyl, n-butyl, i-butyl, tert-butyl, n-pentyl and n-hexyl), a $C_{3-6}$ cycloalkyl group (e.g. cyclopropyl, cyclobutyl, cyclopentyl and cyclohexyl) and a $C_{6-14}$ aryl group (e.g. phenyl and naphtyl).

Preferable examples of "optionally substituted amino group" for A include an amino group which may be substituted with one or two $C_{1-3}$ alkyl groups (e.g. methyl, ethyl and n-propyl).

More preferable examples of $R^6$ and $R^7$ include hydrogen atom and $C_{1-3}$ alkyl (e.g. methyl, ethyl and n-propyl), and, especially hydrogen atom is often used.

m denotes a whole number of one to four. Preferable examples of m are one to two and m=2 is most often the case. n denotes a whole number of one to four. Preferable examples of n are one to two and n=2 is most often the case. Above all, the case where m and n both denote two is most preferable.

Preferable examples of the subject compounds of this invention include the following compounds or salts thereof.

1) 6-(3,3-diethyl-5-sulfamoyl-1-pentyl)imidazo[1,2-b]pyridazine
2) 6-(3,3-diethyl-5-sulfamoyl-1-pentyl)-7-methylimidazo[1,2-b]pyridazine
3) 6-(3,3-pentamethylene-5-sulfamoyl-1-pentyl)imidazo[1,2-b]pyridazine
4) 6-(3,3-pentamethylene-5-sulfamoyl-1-pentyl)-7-methylimidazo[1,2-b]pyridazine
5) 6-(3,3-tetramethylene-5-sulfamoyl-1-pentyl)imidazo[1,2-b]pyridazine
6) 6-(3,3-tetramethylene-5-sulfamoyl-1-pentyl)-7-methylimidazo[1,2-b]pyridazine
7) 6-(3,3-trimethylene-5-sulfamoyl-1-pentyl)imidazo[1,2-b]pyridazine
8) 6-(3,3-trimethylene-5-sulfamoyl-1-pentyl)-7-methylimidazo[1,2-b]pyridazine Among salts of the compound [I] of this invention, pharmaceutically or physiologically acceptable acid addition salts are especially preferable. Examples of such salts include salts with an inorganic acid (e.g. hydrochloric acid, phosphoric acid, hydrobromic acid or sulfuric acid) or salts with an organic acid (e.g. acetic acid, formic acid, propionic acid, fumaric acid, maleic acid, succinic acid, tartaric acid, lactic acid, citric acid, malic acid, oxalic acid, benzoic acid, methanesulfonic acid, p-tolylsulfonic acid or benzenesulfonic acid).

In the following, the method of producing the compound [I] of this invention or its salts is described.

Method A) The compound [I] or its salts of this invention can be obtained by allowing a compound [II] or a salt thereof to react with a compound [III] or a salt thereof.

Y and Z stand for groups capable of leaving by reacting with each other. Specific examples of groups shown by Z include a halogen (e.g. chlorine, bromine, iodine), a $C_{6-10}$ arylsulfonyloxy (e.g. benzenesulfonyloxy, p-tolylsulfonyloxy) and a $C_{1-4}$ alkylsulfonyloxy (e.g. methanesulfonyloxy, trifluoromethanesulfonyloxy). As groups shown by Y, mention is made of metal halide, and, as a halogen (e.g. chlorine, bromine and iodine), iodine is preferably used. Among metals (e.g. zinc and magnesium), zinc is preferably used.

This reaction is preferably conducted by allowing condensation to proceed in the presence of a palladium catalyst. The palladium catalyst means catalysts utilizable for palladium catalyst-cross coupling reaction [those disclosed in Accounts of Chemical Research, 12, 146–151 (1979); ibid 15, 340–348 (1982); Angew. Chem. Int. Ed. Engl. 25, 508–524 (1986), among others], which is exemplified by palladium-tertiary phosphine complex or combination of palladium salt or palladium complex with tertiary phosphine. Palladium-tertiary phosphine complex means a complex of 0-valent or divalent palladium with a tertiary phosphine such as trialkyl phosphine or triaryl phosphine, which is exemplified by tetrakis(triphenylphosphine) palladium, bis(triphenyl phosphine) palladium bromide, bis(triphenyl phosphine) palladium chloride, acetoxybis(triphenyl phosphine) palladium, benzylchlorobis(triphenyl phosphine) palladium, tetrakis(tributyl phosphine) palladium, bis(trimethyl phosphine) palladium chloride, bis(triethyl phosphine) palladium chloride, bis(triproply phosphine) palladium chloride and bis(tributyl phosphine) palladium chloride. Among them, preferable ones include tetrakis(triphenyl phosphine) palladium, bis(triphenyl phosphine) palladium bromide, bis(tripheryl phosphine) palladium chloride and acetoxy bis(triphenyl phosphine) palladium.

The palladium salt means a salt formed by divalent palladium ion and an acid residue, as exemplified by palladium chloride, palladium bromide, palladium acetate, palladium nitrate and palladium sulfate. Among them, palladium chloride, palladium bromide and palladium acetate are preferable.

The palladium complex includes, besides the abovementioned palladium-tertiary phosphine complexes, some other 0-valent or divalent palladium complexes, as exemplified by bis(phenylethylamine) palladium chloride, bis(benzonitrile) palladium chloride, bis(benzonitrile) palladium bromide and bis(acetonitrile) palladium chloride. Among them, bis(benzonitrile) palladium chloride and bis(acetonitrile) palladium chloride are preferably employed.

Examples of tertiary phosphine include triphenyl phosphine, tributyl phosphine, tripropyl phosphine, triethyl phosphine and trimethyl phosphine, and triphenyl phosphine is preferably employed.

This reaction is conducted preferably in a solvent, as exemplified by aromatic hydrocarbons such as benzene, toluene and xylene, ethers such as diethyl ether, tetrahydrofuran and dioxane, amides such as dimethylformamide and dimethyl acetamide, sulfoxides such as dimethyl sulfoxide, and nitriles such as acetonitrile. The reaction temperature ranges from 0° to 200° C., preferably 10° to 100° C. The reaction time ranges from 30 minutes to 24 hours, preferably from 1 to 3 hours. The reaction is conducted advantageously in nitrogen or argon streams. The reaction product can be isolated and purified by conventional means, for example, solvent-extraction, change of pH, phasic transfer, salting out, crystallization, recrystallization and chromatography.

In conducting this reaction, when A' in the general formula [III] is an amino group, it is preferable to protect the amino group by a protective group generally employed in the field of peptide chemistry, for example, protective groups of a type which form amido, e.g. formyl, acetyl or benzoyl; those of a type which form carbamate e.g. tert-butoxycarbonyl or benzyloxycarbonyl; and those of the imino type such as dimethylamino methylene, benzylidene, p-methoxy benzylidene or diphenyl methylene. As preferable protecting groups, use is made of, for example, formyl, acetyl and dimethylamino methylene. Incidentally, when a product obtained by the above-mentioned reaction has a protecting group, the protecting group can be removed by a conventional deprotecting process, for example, hydrolysis with an acid or a base, or catalytic reduction.

Method B) And, a compound [I] or a salt thereof can be obtained by allowing a compound [IV] or a salt thereof to react with a compound [V] or a salt thereof.

This reaction is conducted preferably in an inert solvent as exemplified by alcohols such as methanol and ethanol, ethers such as dioxane and tetrahydrofuran, halogenated hydrocarbons such as dichloromethane and chloroform, acetonitrile and dimethyl sulfoxide. The reaction temperature ranges usually from $-20°$ to $100°$ C., preferably from $-10°$ to $50°$ C. The reaction time ranges usually from 30 minutes to 5 hours, preferably from 1 to 3 hours. The reaction product can be isolated and purified by a conventional method, for example, solvent-extraction, change of pH, phasic transfer, salting out, crystallization, recrystallization or chromatography.

When the compound [I] obtained by the above-mentioned method A) or B) is in the free form, it can be converted, if desired, into a salt by a conventional method. And, when the compound [I] is obtained in the form of salt, it can be converted into its free form or any other salt by a conventional method.

Incidentally, as salts of the starting compounds [II], [III], [IV] and [V] to be employed for producing the compound [I] or its salts, such salts as set forth in reference to the above-mentioned compound [I] can be named. And, these starting compounds [II], [III], [IV], [V] or their salts can be produced by conventional methods or analogous methods thereto or methods described in the following Reference Examples or analogous methods thereto.

Furthermore, the compound [I] of this invention and its pharmaceutically or physiologically acceptable salts have excellent anti-PAF (platelet activating factor) action, which can be used as safe antiasthmatic agents for mammals (man, mouse, dog, rat, cow, etc.). More specifically, in the case of using them as antiasthmatic agents for man, while the dosage varies with age, body weight, symptom, route of administration or dosage time, it is convenient to administer 0.1 to 100 mg/kg/day, preferably 1 to 50 mg/kg/day, more preferably 5 to 50 mg/kg/day, in two to three installments. The administration route may be either oral or non-oral.

While the compound [I] or salts thereof may be administered as they are, i.e. in powdery state, they are administered usually in the form of pharmaceutical compositions prepared by using carriers for such composition. Examples of such compositions include granule, micro-granule, powder, syrup, injection and inhalation. These compositions can be prepared by conventional methods. As carriers of compositions for oral administration, conventional ones used in the field of pharmaceutical compositions, for example, starch, mannitol, crystalline cellulose and carboxymethyl cellulose sodium, are employed. As carriers of injections, use is made of, for example, distilled water, physiological saline, a glucose solution and infusion. Besides, additives generally used in the preparation of pharmaceutical compositions can be supplemented upon necessity.

[EXAMPLES]

(Examples and Reference Examples)

This invention is illustrated in further detail in the Reference Examples, Examples Formulation Example and Experiment, which are only examples, and do not limit this invention. Modification within the scope of this invention are permissible.

Elution in a column chromatography in the Reference Examples and Examples was conducted while monitoring with TLC (Thin Layer Chromatography). In the TLC monitoring, the TLC plate used was $60F_{254}$ manufactured by Merck Co., the developing solvent was the same as the one used for eluting in the column chromatography, and the detection was conducted with a UV detector. The silica gel for the column was silica gel 60 manufactured by Merck Co., (70–230 mesh).

Further, room temperature means $15°-25°$ C.

Abbreviations used in the Reference Examples and Examples have the following meanings.

J:coupling constant Hz:hertz
s:singlet d:doublet
t:triplet
q:quartet
m:multiplet
NMR:Nuclear Magnetic Resonance
DMSO:Dimethyl sulfoxide
$CDCl_3$:deuteriochloroform
v/v:volume/volume
%:weight %
m.p.:melting point
i.v.:intravenous injection
δ (ppm):chemical shift Reference Example 1

Production of 3-aminosulfonyl-1-iodopropane 10.76 g of 3-aminosulfonyl-1-chloropropane was dissolved in 150 ml of acetone. To the solution was added 20.46 g of sodium iodide, and the mixture was heated for 15 hours under reflux. The reaction mixture was concentrated under reduced pressure. The residue was dissolved in water, which was extracted with ethylacetate. The extract was washed with water and dried over magnesium sulfate. The solvent was distilled off. The resulting crystals were collected by filtration to give 15.06 g of the titled compound.

NMR ($d_6$-DMSO) δ: 2.0–2.3(2H,m), 3.06(2H,t,J=8Hz), 3.37(2H,t,J=8Hz), 6.89(2H,s).

Reference Example 2

Production of 4-aminosulfonyl-1-iodobutane

Using 4-aminosulfonyl-1-chlorobutane in place of 3-aminosulfonyl-1-chloropropane in Reference Example 1, substantially the same reaction as in Reference Example 1 was conducted to produce the titled compound.

NMR($CDCl_3$) δ: 1.8–2.2(4H,m), 3.0–3.3(4H,m), 4.68(2H,s).

Reference Example 3

Production of 5-bromo-3,3-dimethylpentane-1-thiocyanate 17.3 g of 1,5-dibromo-3,3-dimethylpentane was dissolved in 100 ml of dimethylformamide. To the solution was added 6.84 g of potassium thiocyanate, and the mixture was stirred for 2 hours at 80° C. The reaction mixture was cooled, to which was added 400 ml of ice-water, followed by extraction with ethyl acetate. The extract was dried over magnesium sulfate, from which the solvent was distilled off. The residue was subjected to silica gel column chromatography, eluting with hexane:ethyl acetate (19:1) to give 7.81 g of the titled compound.

NMR(CDCl$_3$) δ: 0.97(6H,s), 1.7–2.0(4H,m), 2.8–3.0(2H,m), 3.3–3.5(2H,m).

Reference Example 4

Production of 5-aminosulfonyl-3,3-dimethyl-1-bromopentane

Chlorine gas was bubbled in a mixture of 4.0 g of 5-bromo-3,3-dimethylpentane-1-thiocyanate, 30 ml of acetic acid and 30 ml of water under ice cooling with stirring for 75 minutes. The solution was then stirred for 30 minutes at room temperature, to which was added 100 ml of ice-water, followed by extraction with dichloromethane. The extract was washed with water, then dried over magnesium sulfate, from which was distilled off the solvent. The residue was dissolved in 50 ml of dichloromethane, into which was introduced ammonia gas for 45 minutes while stirring under ice cooling with ice. The reaction mixture was then stirred for 30 minutes at room temperature. The precipitate was removed by filtration. The filtrate was concentrated and subjected to silica gel column chromatography, eluting with dichloromethane:methanol (40:1) to give 3.36 g of the titled compound.

NMR(CDCl$_3$) δ: 0.97(6H,s), 1.7–2.0(4H,m), 3.0–3.2(2H,m), 3.3–3.5(2H,m), 4.65(1H,s)

Reference Example 5

Production of 5-aminosulfonyl-3,3-dimethyl-1-iodopentane

In 80 ml of acetone was dissolved 5.41 g of 5-aminosulfonyl-3,3-dimethyl-1-bromopentane. To the solution was added 7.85 g of sodium iodide, and the mixture was heated for 3 hours under reflux. The reaction mixture was concentrated under reduced pressure. The residue was dissolved in water, followed by extraction with ethyl acetate. The extract was washed with water, dried over magnesium sulfate, then the solvent was distilled off. Resulting crystals were collected by filtration to give 6.2 g of the titled compound.

NMR(CDCl$_3$) δ: 0.94(6H,s), 1.7–2.0(4H,m), 3.0–3.2(4H,m), 4.66(2H,s)

Reference Example 6

Production of 5-(N,N-dimethylaminomethylene)aminosulfonyl-3,3-dimethyl-1-iodopentane 6.3 g of 5-aminosulfonyl-3,3-dimethyl-1-iodopentane was dissolved in 50 ml of benzene. To the solution was added 3.1 ml (23.4 mmol) of N,N-dimethylformanide dimethylacetal.

The mixture was stirred for one hour at room temperature. The reaction mixture was concentrated under reduced pressure. The residue was subjected to column chromatography on 150 g of silica gel, eluting with ethyl acetate: hexane (4:1,v/v) to give 7.24 g of the titled compound as a colorless crystal.

m.p. 105°–106° C.

Elemental Analysis for C$_{10}$H$_{21}$N$_2$O$_2$SI
Calcd. (%): C, 33.34; H, 5.88; N, 7.78
Found (%): C, 33.57; H, 5.79; N, 8.09

$^1$H-NMR(CDCl$_3$)δ: 0.91(6H, s), 1.65–1.78(2H, m), 1.84–1.98(2H, m), 2.91–3.03(2H, m), 3.05(3H, s), 3.14(3H, s), 3.06–3.19(2H, m), 8.05(1H, s).

Reference Example 7

Production of 1-cyano-5-(N,N-dimethylaminomethylene)-aminosulfonyl-3,3-dimethylpentane A mixture of 7.20 g of the iodo-compound obtained in the Reference Example 6, 1.95 g of potassium cyanide, 0.26 g(1.0 mmol) of 18-crown-6 and 100 ml of dimethyl sulfoxide were stirred for 5 hours at 90° C.

The reaction mixture was diluted with water, followed by extraction with ethyl acetate. The extract was washed with water, dried over magnesium sulfate, then the solvent was distilled off. The residue was subjected to silica gel column chromatography having 100 g of silica gel, eluting with ethyl acetate:chloroform (5:1, v/v) to give 4.23 g (82%) of the titled compound as a colorless oily product.

NMR(CDCl$_3$)δ: 0.94(6H, s), 1.57–1.80(4H, m), 2.32(2H, t,J=7.6 Hz), 2.91–3.04(2H, m), 3.05(3H, s), 3.15(3H, s), 8.05(1H, s).

Reference Example 8

Production of methyl 4,4-dimethyl-6-sulfamoylhexanoate

A mixture of 3.6 g of 1-cyano-5-(N,N-dimethylaminomethylene)aminosulfonyl-3,3-dimethylpentane and 30 ml of concentrated hydrochloric acid were stirred for 11 hours at 110°–115° C. The reaction mixture was concentrated to dryness.

The resulting carboxylic acid was dissolved in 50 ml of methanol, to which was added 0.3 ml of concentrated sulfonic acid, and the solution was heated for 6 hours under reflux. The reaction mixture was concentrated under reduced pressure. To the residue was added water, which then was extracted by chloroform. The extract was dried over magnesium sulfate, then the sovent was distilled off. The residue was subjected to silica gel column chromatography, eluting with ethyl acetate:hexane (2:1) to give 2.95 g of the titled compound.

NMR(CDCl$_3$)δ: 0.93(6H, s), 1.54–1.85(4H, m), 2.30(3H, t, J=8.0 Hz), 3.10(2H, d t, J=8.0 Hz), 3.68(3H, s), 4.89(2H, br s).

Reference Example 9

Production of 6-(N,N-dimethylaminomethylene)amunosulfonyl-3,3-dimethylhexanol (1) To a tetrahydrofuran suspension (100 ml) of lithium aluminum hydride (0.79 g) was added dropwise a tetrahydrofuran solution (20 ml) of methylester (3.30 g) obtained in the reference example 8 with stirring under ice cooling.

Then the stirring was continued for further 40 minutes at the same temperature. To the reaction mixture was added water dropwise. The mixture was made acidic with 2N hydrochloric acid. The organic layer was washed with water, dried over magnesium sulfate.

The solvent was distilled off to give 3.08 g of an oily residue. The residue was used for following reaction without purification.

(2) The oily residue obtained above (1) was dissolved in 50 ml of toluene, to which was added 1.85 ml of N,N-dimethylformamide dimethylacetal. The mixture was stirred for one hour at 80° C. The reaction mixture was concentrated. The residue was subjected to silica gel column chromatography, eluting with chloroform- :methanol (20:1) to give 3.15 g of the titled compound as an oily product.

IR(Neat): 3480, 1630 cm¹.

NMR(CDCl₃)δ: 0.90(6H, s), 1.20–1.33(2H, m), 1.46–1.78(4H, m), 1.61(1H, s), 2.98(2H, d t, J=6.4 Hz), 3.05(3H, s), 3.14(3H, s), 3.62(2H, t, J=6.4 Hz), 8.04(1H, s).

Reference Example 10

Production of 6-(N,N-dimethylaminomethylene)aminosulfonyl-1-iodo-3,3-dimethylhexane (1) 3.10 g of the alcohol obtained in the reference example 9 was dissolved in 50 ml of dichlormethane. To the mixture was added dropwise 2.76 ml of trifluoromethane sulfonic acid anhydride with stirring under ice cooling.

The reaction mixture was stirred for 30 minutes under ice cooling, to which was added 2,6-lutidine, further stirred for 30 minutes.

To the reaction mixture was added water, which was extracted with dichloromethane.

The extract was washed with an aqueous solution of potassium hydrogensulfate solution and further brine and dried over magnesium sulfate. Then the solvent was distilled off to give an oily residue which was used for following reaction without purification. The residue was dissolved in 50 ml of acetone, to which was added 5.26 g of sodium iodide. The mixture was heated for two hours under reflux with stirring.

The reaction mixture was cooled, to which was added water, followed by extraction with ethyl acetate.

The extract was washed with water and dried over magnesium sulfate. The solvent was distilled off.

The residue was subjected to silica gel column chromatography having, 80 g of silica gel, eluting with ehtyl acetate: hexane (3:1) to give 3.14 g of the titled compound which was crystalized from isopropylether.

mp 67°–68° C.

Elemental Analysis for $C_{11}H_{23}IN_2O_3S$:

Calcd. (%): C,35.30; H,6.19; N,7.48;
Found (%): C,35.64; H,6.20; N,7.72;

NMR(CDCl₃)δ: 0.90(6H, s), 1.23–1.36(2H, m), 1.60–1.90(4H, m), 2.93–3.21(4H, m), 3.05(3H, s), 3.14(3H, s), 8.05(1H, s).

EXAMPLE 1

Production of 6-(3-sulfamoylpropyl)imidazo [1,2-b]pyridazine

In 10 ml of toluene was suspended 1.25 g of 3-aminosulfonyl-1-iodopropane. To the suspension was added 0.731 ml of dimethylformamide dimethyl acetal, and the mixture was stirred for 30 minutes. The mixture was concentrated under reduced pressure. The residue was dissolved in a mixture of 10 ml of toluene and 1 ml of dimethyl acetamide. To the solution was added, under nitrogen atmosphere, 0.491 g of zinc activated with copper. The mixture was stirred for 2 hours at 80° C. The reaction mixture was cooled to room temperature, to which were added 0.615 g of 6-chloroimidazo[1,2-b]pyridazine and 56 mg of bis(triphenylphosphine)palladium (II) chloride. The mixture was stirred for 1.5 hour at 80° C. under nitrogen atmosphere. The reaction mixture was cooled, to which were then added 10 ml of ice-water and 10 ml of 1N hydrochloric acid. The aqueous layer was separated, to which was added an aqueous solution of sodium hydrogen carbonate to adjust the pH to 6, followed by extraction with ethyl acetate-tetrahydrofuran (1:1). The extract was dried over magnesium sulfate, from which the solvent was distilled off, The residue was subjected to silica gel column chromatography, eluting with dichloromethane:ethyl acetate:methanol=10:10:4. The corresponding fractions were collected and concentrated. The residue (0.72 g) was dissolved in 25 ml of 5N hydrochloric acid. The solution was heated for 20 minutes under reflux. The reaction mixture was cooled, which was then concentrated under reduced pressure. To the residue was added an aqueous solution of sodium hydrogen carbonate to adjust the pH to 6, which was saturated with sodium chloride, followed by extraction with ethyl acetate:tetrahydrofuran (1:2). The extract was dried over magnesium sulfate, from which the solvent was distilled off. The residue was subjected to silica gel column chromatography, eluting with a 5%(v/v) methanol-dichloromethane solution. The corresponding fractions were collected and concentrated to give 0.302 g of the titled compound. m.p.210°–213° C.

Elemental Analysis for $C_9H_{12}N_4O_2S$:

Calcd.(%): C, 44.99; H, 5.03; N, 23.32;
Found (%): C, 44.72; H, 5.12; N, 22.91.

NMR(d₆-DMSO) δ: 2.0–2.3(2H,m), 2.9–3.2(4H,m), 6.80(2H,s), 7.18,8.05(each 1H,d,J=9Hz), 7.72,8.21(each 1H,s)

EXAMPLE 2

Production of 6-(4-sulfamoyl-1-butyl)imidazo[1,2-b]pyridazine

Using 4-aminosulfonyl-1-iodobutane in place of 3-aminosulfonyl-1-iodopropane in Example 1, substantially the same reaction was conducted as in Example 1 to produce the titled compound. m.p. 167°–175° C.

Elemental Analysis for $C_{10}H_{14}N_4O_2S$:

Calcd.(%): C, 47.23; H, 5.55; N, 22.03;
Found (%): C, 47.01; H, 5.40; N, 22.15.

NMR(d₆-DMSO) δ: 1.6–2.0(4H,m), 2.7–3.1(4H,m), 6.75(2H,s), 7.25,8.11(each 1H,d,J=10Hz), 7.72,8.23(each 1H,d,J=1Hz)

EXAMPLE 3

Production of 6-(3,3-dimethyl-5-sulfamoyl-1-pentyl)imidazo[1,2-b]pyridazine

In 15 ml of toluene was suspended 2.45 g of 5-aminosulfonyl-3,3-dimethyl-1-iodopentane. To the suspension was added 1.17 ml of dimethylformamide dimethyl acetal, and the mixture was stirred for 30 minutes at room temperature. The reaction mixture was concentrated under reduced pressure. The residue was dissolved in a mixture of 20 ml of toluene and 2 ml of dimethyl acetamide. To the solution was added 0.785 g of zinc activated with copper. The mixture was stirred for 1.5 hour at 80° C. The reaction mixture was cooled to room temperature, to which were added 1.23 g of 6-chloroimidazo [1,2-b]pyridazine and 112 mg of bis(triphenylphosphine) palladium (II) chloride. The mixture was stirred for 1.5 hour at 80° C. under nitrogen atmosphere. The reaction mixture was cooled, to which were added 15 ml of ice-water and 12 ml of 1N hydrochloric acid. Insolubles were filtered off, and the aqueous layer was taken. To the aqueous layer was added an aqueous solution of sodium hydrogen carbonate to adjust the pH to 6, which was subjected to extraction with ethyl acetate-tetrahydrofuran (3:1). The extract was dried over magnesium sulfate, then the solvent was distilled off. The residue was subjected to silica gel column chromatography, eluting with 5% (v/v) methanol-dichloromethane solution. The corresponding fractions were collected and concentrated, and 1.56 g of the residue was dissolved in 30 ml of 5N hydrochloric acid. The solution was heated for 30 minutes under reflux. The reaction mixture was concentrated under reduced pressure. To the residue was added an aqueous solution of sodium hydrogen carbonate to adjust the pH to 7, followed by extraction with ethyl acetate - tetrahydrofuran (3:1). The extract was dried over magnesium sulfate, then the solvent was distilled off. The residue was subjected to silica gel column chromatography, eluting 7% (v/v) methanol-dichloromethane. The corresponding fractions were collected and concentrated to give 0.712 g of the titled compound. m.p. 152° C.

Elemental Analysis for $C_{13}H_{20}N_4O_2S$:
Calcd.(%): C, 52.68; H, 6.80; N, 18.90;
Found (%): C, 52.79; H, 6.98; N, 18.70.
NMR($d_6$-DMSO) δ: 0.96(6H,s), 1.5–1.9(4H,m), 2.7–3.1(4H,m), 6.78(2H,s), 7.23,8.07(each 1H,d,J=9Hz), 7.71,8.22(each 1H,s)

EXAMPLE 4

Production of 6-(3,3-dimethyl-5-sulfamoyl-1-pentyl)-7-methylimidazo[1,2-b]pyridazine In 60 ml of toluene was suspended 7.90 g of 5-aminosulfonyl-3,3-dimethyl-1-iodopentane, to which was added 4.19 ml of dimethylformamide dimethylacetal. The mixture was stirred for 30 minutes at room temperature. The reaction mixture was concentrated under reduced pressure. The residue was dissolved in a mixture of 150 ml of toluene and 15 ml of hexamethyl phosphoric triamide. To the solution was added 3.93 g of zinc activated with copper under nitrogen atmosphere, and the mixture was stirred for 1.5 hour at 80° C. The reaction mixture was cooled to room temperature, to which were added 4.02 g of 6-chloro-7-methylimidazo[1,2-b]pyridazine and 0.84 g of bis(triphenylphosphine) palladium (II), and the mixture was stirred for 2 hours at 80° C. under nitrogen atmosphere. The reaction mixture was cooled, to which were added 200 ml of ethyl acetate, 80 ml of water and 40 ml of 25% aqueous ammonia under ice cooling, and the mixture was stirred for 30 minutes. Insolubles were filtered off, and the aqueous layer was subjected to extraction with ethyl acetate three times. The extract was washed with aqueous saline solution and dried over magnesium sulfate, from which the solvent was distilled off. The residue was subjected to silica gel column chromatography, eluting with a mixture of dichloromethane and methanol (35:1). The corresponding fractions were collected and concentrated. 3.3 g of the residue was dissolved in 100 ml of 5N hydrochloric acid, and the solution was heated for 45 minutes under reflux. The reaction mixture was cooled, which was then concentrated under reduced pressure. To the residue was added an aqueous solution of sodium hydrogen carbonate to adjust the pH to 7, followed by extraction with ethyl acetate. The extract was washed with an aqueous saline solution, followed by drying over magnesium sulfate. The solvent was distilled off, and the residue was subjected to silica gel column chromatography, eluting with dichloromethane:methanol (15:1). The corresponding fractions were collected and concentrated to give 2.55 g of the titled compound.
m.p.170° to 172° C.

Elemental Analysis for $C_{14}H_{22}N_4O_2S$:
Calcd.(%): C, 54.17; H, 7.14; N, 18.05;
Found (%): C, 53.86; H, 7.11; N, 17.76.
NMR($d_6$-DMSO) δ: 0.96(6H,s), 1.5–1.9(4H,m), 2.6–3.1(4H,m), 2.37(3H,s), 6.77(2H,s), 7.60(1H,s), 7.84(1H,s), 8.11(1H,s)

EXAMPLE 5

Production of 7,8-dimethyl-6-(3,3-dimethyl-5-sulfamoyl-1-pentyl)imidazo[1,2-b]pyridazine Using 6-chloro-7,8-dimethylimidazo[1,2-b]pyridazine in place of 6-chloroimidazo[1,2-b]pyridazine in Example 3, substantially the same reaction as in Example 3 was conducted to produce the titled compound. m.p.160°–163° C.

Elemental Analysis for $C_{15}H_{24}N_4O_2S$:
Calcd.(%): C, 55.53; H, 7.46; N, 17.2;
Found (%) C, 55.35; H, 7.40; N, 16.98.
NMR($d_6$-DMSO) δ: 0.98(6H,s), 1.4–1.8(4H,m), 2.29(3H,s), 2.52(3H,s), 2.7–3.1(4H,m), 6.77(2H,s), 7.59,8.08(each 1H,d,J=1Hz)

EXAMPLE 6

Production of 6-(3,3-dimethyl-5-sulfamoyl-1-pentyl)-8-methylimidazo[1,2-b]pyridazine In 10 ml of toluene was suspended 1.53 g of 5-aminosulfonyl-3,3-dimethyl-1-iodopentane. To the suspension was added 0.74 ml of dimethylformamide dimethyl acetal. The mixture was stirred for 30 minutes at room temperature. The reaction mixture was concentrated under reduced pressure. The residue was dissolved in a mixture of 13 ml of toluene and 1.3 ml of dimethyl acetamide. To the solution was added 0.654 g of zinc activated with copper, and the mixture was stirred for 2.5 hours at 80° C. under nitrogen atomosphere. The reaction mixture was cooled to room temperature, to which were added 0.755 g of 6-chloro-8-methylimidazo[1,2-b]pyridazine and 64 mg of bis(triphenylphosphine)palladium (II) chloride. The mixture was stirred for 2 hours at 80° C. under nitrogen atmosphere. The reaction mixture was cooled, to which were added 10 ml of ethyl acetate, 10 ml of ice-water and 7.5 ml of a 25% aqueous ammonia, followed by stirring for 30 minutes at room temperature. Insolubles were filtered off. To the aqueous layer was added 3 g of sodium chloride, which was subjected to extraction with ethyl acetate three times. The extract was washed with an aqueous saline solution and dried over magnesium sulfate. The solvent was distilled off, and the residue was subjected to silica gel column chromatography, eluting with dichloromethane:methanol (30:1). The corresponding fractions were combined and concentrated. The residue (0.802 g) was dissolved in 25 ml of 5N hydrochloric acid, and the solution was heated for one hour under reflux. The reaction mixture was cooled and concentrated under reduced pressure. To the residue was added water to adjust the pH to 7, followed by extraction with ethyl acetate. The extract was dried over magnesium sulfate, then the solvent was distilled off. The residue was subjected to silica gel column chromatography, eluting with dichloromethane:methanol (15:1). The corresponding fractions were concentrated to give 0.527 g of the titled compound. m.p.136°–138° C.

Elemental Analysis for $C_{14}H_{22}N_4O_2S$:
Calcd.(%): C, 54.17; H, 7.14; N, 18.05;
Found (%): C, 54.13; H, 7.25; N, 17.82.
NMR($d_6$-DMSO) δ: 0.96(6H,s), 1.5–1.8(4H,m), 2.53(3H,s), 2.6–3.1(4H,m), 6.77(2H,s), 7.03(1H,s), 7.62,8.12(each 1H,d,J=1Hz)

EXAMPLE 7

Production of 7,8-dimethyl-6-(3,3-dimethyl-5-sulfamoyl-1-pentyl)[1,2,4]triazolo(1,5-b]pyrida zine Using 6-chloro-7,8-dimethyl[1,2,4]triazolo[1,5-b]pyridazine in place of 6-chloro-8-methylimidazo[1,2-b]pyridazine in Example 6, substantially the same reaction as in Example 6 was conducted to produce the titled compound. m.p.90° C.

Elemental Analysis for $C_{14}H_{23}N_5O_2S\cdot0.4H_2O$:
Calcd.(%): C, 50.55; H, 7.21; N, 21.06;
Found (%): C, 50.88; H, 7.27; N, 20.86.
NMR($d_6$-DMSO) δ: 0.99(6H,S), 1.5–1.9(4H,m), 2.37(3H,s), 2.57(3H,s), 2.7–3.1(4H,m), 6.77(2H,s), 8.46(1H,s)

EXAMPLE 8

Production of 6-(3,3-dimethyl-5-sulfamoyl-1-pentyl)-7-methyl[1,2,4]triazolo[1,5-b]pyrid azine Using 6-chloro-7-methyl [1,2,4] triazolo [1,5-b] pyridazine in place of 6-chloro-8-methylimidazo [1,2-b] pyridazine in Example 6, substantially the same reaction as in Example 6 was conducted to produce the titled compound. m.p. 191°–193° C.

Elemental Analysis for $C_{14}H_{21}N_5O_2S\cdot0.2H_2O$:
Calcd.(%): C, 49.57; H, 6.85; N, 22.23;
Found (%): C, 49.50; H, 6.81; N, 22.18.
NMR($d_6$-DMSO) δ: 0.99(6H,s), 1.5–1.8(4H,m), 2.49(3H,d,J=1Hz), 2.7–3.1(4H,m), 6.77(2H,s), 8.17(1H,q,J=1Hz), 8.50(1H,s)

EXAMPLE 9

Production of 6-(3,3-dimethyl-5-sulfamoyl-1-pentyl) [1,2,4] triazolo [1,5-b] pyridazine Using 6-chloro [1,2,4] triazolo [1,5-b ] pyridazine in place of 6-chloro-8-methylimidazo[1,2-b]pyridazine in Example 6, substantially the same reaction as in Example 6 was conducted to produce the titled compound. m.p.165°–168° C.

Elemental Analysis for $C_{12}H_{19}N_5O_2S$:
Calcd.(%): C, 48.47; H, 6.44; N, 23.55;
Found (%): C, 48.82; H, 6.61; N, 23.07.
NMR($d_6$-DMSO) δ: 0.97(6H,s), 1.5–1.8(4H,m), 2.7–3.1(4H,m), 6.76(2H,s), 7.65,8.36(each 1H,d,J=9Hz), 8.58(1H,s)

EXAMPLE 10

Production of 7-methyl-6-(4-sulfamoyl-1-butyl-)imidazo [1,2-b] pyridazine

Using 4-aminosulfonyl-1-iodobutane in place of 5-aminosulfonyl-3,3-dimethyl-1-iodopentane in Example 6, and, using 6-chloro-7-methylimidazo [1,2-b] pyridazine in place of 6-chloro-8-methylimidazo [1,2-b] pyridazine, substantially the same reaction as in Example 6 was conducted to produce the titled compound. m.p.166°–173° C.

Elemental Analysis for $C_{11}H_{16}N_4O_2S$:
Calcd.(%): C, 49.24; H, 6.01; N, 20.88;
Found (%): C, 49.35; H, 6.23; N, 20.62.
NMR($d_6$-DMSO) δ: 1.6–2.0(4H,m), 2.36(3H,s), 2.7–3.2(4H,m), 6.77(2H,s), 7.60(1H,s), 7.84,8.09(each 1H,s)

EXAMPLE 11

Production of 6-(3,3-dimethyl-5-sulfamoyl-1-pentyl) imidazo [1,2-b] pyridazine hydrochloride In 30 ml of methanol was dissolved 0.637 g of 6-(3,3-dimethyl-5-sulfamoyl-1-pentyl)imidazo [1,2-b] pyridazine produced in Example 3. To the solution was added 2.4 ml of 1N hydrochloric acid, and the mixture was subjected to filtration. The filtrate was concentrated under reduced pressure. Resulting crystals were collected to give 0.707 g of the titled compound. m.p.181°–185° C.

Elemental Analysis for $C_{13}H_{21}ClN_4O_2S$:
Calcd.(%): C, 46.91; H, 6.36; N, 16.83;
Found (%): C, 46.79; H, 6.35; N, 16.63.
NMR($d_6$-DMSO) δ: 0.97(6H,s), 1.5–1.8(4H,m), 2.8–3.1(4H,m), 6.78(2H,s), 7.79,8.41(each 1H,d,J=9Hz), 8.28,8.62(each 1H,d,J=2Hz)

EXAMPLE 12

Production of 6-(3,3-dimethyl-5-sulfamoyl-1-pentyl)-7-methylimidazo [1,2-b] pyridazine hydrochloride In 25 ml of ethanol was suspended 0.25 g of 6-(3,3-dimethyl-5-sulfamoyl-1-pentyl)-7-methylimidazo [1,2-b] pyridazine. The suspension was dissolved by the addition of 1N hydrochloric acid, which was subjected to filtration, followed by concentrated under reduced pressure. The residue was crystallized from ethyl ether to give 0.267 g of the titled compound.
m.p.193°–196° C.

Elemental Analysis for $C_{14}H_{23}ClN_4O_2S$:
Calcd.(%): C, 48.48; H, 6.68; N, 16.15;
Found (%): C, 48.56; H, 6.89; N, 15.88.
NMR($d_6$-DMSO) δ: 0.99(6H,s), 1.5–1.9(4H,m), 2.54(3H,s), 2.8–3.1(4H,m), 6.79(2H,s), 8.23,8.56(each 1H,d,J=2Hz), 8.26(1H,s)

EXAMPLE 13

Production of 6-(4,4-dimethyl-6-sulfamoyl-1-hexyl)-7-methylimidozo[1,2-b]pyridazine 1.30 g of 6-(N,N-dimethylaminomethylene)aminosulfonyl-1-iodo-3,3-dimethylhexane was dissolved in a mixture of 20 ml of toluene and 2.0 ml of N,N-dimethylacetoamide. To the solution was added 0.72 g of zinc activated with copper, and the mixture was stirred for 2 hours at 90° C. under nitrogen atomosphere.

The reaction mixture was cooled to room temperature, to which were added 0.50 g of 6-chloro-7-methylimidazo[1,2-b]pyridazine and 60 mg of bis(triphenylphosphine)palladium (II) chloride. The mixture was stirred for 2 hours at 90° C. under nitrogen atmosphere. The reaction mixture was cooled, to which were added 5 ml of a 28% ammonia solution and 12 ml of water. Insolubles were filtered off with celite. The filtrate was extracted with ethyl acetate. The extract was washed with water and dried over magnesium sulfate. The solvent was distilled off. The residue was subjected to silica gel column chromatography, eluting with chloroform:methanol (40:1) to give 0.32 g of an oily product.

A mixture of the obtained oily product and 7 ml of 6N hydrochloric acid was heated at 100° C. for 40 minutes with stirring. The reaction mixture was concentrated, neutralized with saturated sodium hydrogencarbonate and extracted with ethyl acetate:tetrahydrofuran (3:1). The extract was washed with water and dried over magnesium sulfate. The solvent was distilled off. The residue was subjected to silica gel column chromatography, eluting with chloroform:methanol (20:1) to give the product, which was crystallized from ethylether to give 34 mg of the titled compound.
m.p. 141°–142° C.

Elemental Analysis for $C_{15}H_{24}N_4O_2S$:
Calcd. (%): C,55.53; H,7.46; N,17.27;

Found (%): C,55.31; H,7.66; N,17.20.

NMR(DMSO-d₆)δ: 0.89(6H, s), 1.23-1.39(2H, m), 1.53-1.79(4H, m), 2.35(3H, s), 2.78(2H, t, J=7.0 Hz), 2.89-3.04(2H, m), 6.75(2H, br s), 7.60(1H, s), 7.83(1H, s), 8.11(1H, s).

Formulation Example

| (a) Coated tablets | |
|---|---|
| Compound of Example 1 | 10.0 mg |
| Lactose | 60.0 mg |
| Corn starch | 35.0 mg |
| Gelatin | 3.0 mg |
| Magnesium stearate | 2.0 mg |

Method

A mixture of the compound obtained in Example 1, lactose and corn starch was granulated, using a 10% aqueous solution of gelatin, through a 1 mm mesh screen. The granules were dried at 40° C. and screened again. The granules thus obtained were blended with magnesium stearate and compressed. The core tablets thus obtained were coated with an aqueous suspension of sucrose, titanium dioxide, talc and gum arabica. The coated tablets were polished with bees wax.

| (b) Tablets | |
|---|---|
| Compound of Example 1 | 10.0 mg |
| Lactose | 70.0 mg |
| Corn starch | 50.0 mg |
| Soluble starch | 7.0 mg |
| Magnesium stearate | 3.0 mg |
| | 140.0 mg |

A mixture of the compound obtained in Example 1 and magnesium stearate was granulated with an aqueous solution of soluble starch. The granules were dried and blended with lactose and corn starch. The mixture was compressed to yield tablets

| (c) Injectable solution | |
|---|---|
| Compound of Example 1 | 5.0 mg |
| Common salt | 20.0 mg |
| Distilled water | to 2 ml |

The compound obtained in Example 1 and excipients were dissolved in distilled water, to which was added water to give a pre-determined concentration. The solution was subjected to filtration, and the filtrate was filled in 2 ml ampoule under aseptic conditions. The ampoule was sterilized and sealed. The content of the compound of Example 1 in one ampoule was 5 mg.

Experiment

Pharmacological test results on the compound (I) and salts thereof are shown below. (Action against PAF-induced bronchoconstriction in guinea pigs)

Male Hartley guinea pigs (body weight 500 g) were used. The bronchoconstriction reaction in the guinea pig which has intravenously received PAF (1 μg/kg) was measured by the Konzett-Rōessler method. The trachea of the guinea pig with its back fixed was incised under anesthesia condition with urethane (intraperitoneal injection, 1.50 g/Kg) and connected with an artificial respirator via a cannula. The branch of the tracheal cannula was connected with a transducer (7020 type, Ugobasile). Air was sent to the trachea at the volume of 3-7 ml/stroke, at the stroke of 70 strokes/min. at load pressure of 10cm H₂O to lung and overflowed air volume was recorded with Rectegraph (Recte-Hori-8s, Sanei Sokuki) via the transducer. After the guinea pig was treated with galamine (1 mg/Kg, i.v.), PAF (1 μg/Kg) dissolved in a physiological saline solution was administered to the guinea pig via a jugular venous cannula and the bronchoconstriction reaction induced thereby was recorded for 15 minutes. The drug (10 mg/Kg) suspended in a 5% gum arabic solution was administered orally 1 hour before the injection of PAF. The results are shown in the following Table I. Table 1

Action against PAF-induced bronchoconstriction of guinea pigs

| Example No. | Inhibition (%) of PAF-induced bronchoconstriction |
|---|---|
| 4 | 86 |

From the above table, it is understood that the compound [I] of this invention or salts thereof have an excellent action of controlling bronchoconstriction and are excellent antiasthmatic agents.

What is claimed is:

1. A compound represented by the formula:

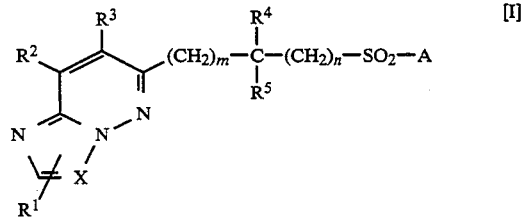

[I]

wherein X stands for the group —CH= or a nitrogen atom; $R^1$ stands for (i) a hydrogen atom, (ii) a straight chain or branched $C_{1-6}$ alkyl group which may be substituted with one to four substituents selected from the group consisting of hydroxy, amino, carboxy, nitro, mono- or di-$C_{1-6}$ alkyl amino, $C_{1-6}$ alkoxy, $C_{1-6}$ alkylcarbonyloxy and halogen or (iii) a halogen atom; $R^2$ and $R^3$ respectively stand for (i) a hydrogen atom or (ii) a straight chain or branched $C_{1-6}$ alkyl group which may be substituted with one to four substituents selected from the group consisting of hydroxy, amino, carboxy, nitro, mono- or di-$C_{1-6}$ alkyl amino, $C_{1-6}$ alkoxy, $C_{1-6}$ alkylcarbonyloxy and halogen; $R^4$ and $R^5$ respectively stand for (i) a hydrogen atom or (ii) a straight chain or branched $C_{1-6}$ alkyl group which may be substituted with one to four substituents selected from the group consisting of hydroxy, amino, carboxy, nitro, mono- or di-$C_{1-6}$ alkyl amino, $C_{1-6}$ alkoxy, $C_{1-6}$ alkylcarbonyloxy and halogen, or (iii), taken together, form a $C_{3-7}$ cycloalkane, $C_{3-7}$ cycloalkene, oxetane, tetrahydrofuran, tetrahydropyran, azetidine, pyrrolidine, piperidine, piperazine, tetrahydrothiophene, homopiperidine or morpholine, each of which may be substituted with one to five substituent(s) selected from the group consisting of (a) a $C_{1-6}$ alkyl group which may be substituted with one to four substituents(s) selected from the group consisting of a hydroxyl, an amino, a mono-or di- $C_{1-6}$ alkylamino, a $C_{1-6}$ alkoxy, a $C_{1-6}$ alkylcarbonyloxy and a (b) an amino group which may be substituted with one or two substituent(s) selected from the group consisting of a $C_{1-6}$ alkyl, a $C_{1-6}$ acyl, a pyrrolidino, a morpholino, a piperidino and a 1-piperazinyl, (c) a hydroxy, (d) a carboxy, (e) a nitro, (f) a $C_{1-6}$ alkoxy and (g) a halogen; A stands for a group of

wherein $R^6$ and $R^7$ respectively stand for (i) a hydrogen atom, (ii) a $C_{1-6}$ alkyl group which may be substituted with one to four substituents selected from the group consisting of hydroxy, amino, carboxy, nitro, mono- or di-$C_{1-6}$ alkylamino, $C_{1-6}$ alkoxy, $C_{1-6}$ alkylcarbonyloxy and halogen atom, (iii) a $C_{3-6}$ cycloalkyl group which may be substituted with one to four substituents selected from the group consisting of hydroxy, amino, carboxy, nitro, mono- or di-$C_{1-6}$ alkylamino, $C_{1-6}$ alkoxy, $C_{1-6}$ alkylcarbonyloxy and halogen atom, (iv) a phenyl or naphthyl group which may be substituted with one to five substituents selected from the group consisting of $C_{1-6}$ alkyl, amino, acetamido, hydroxy, carboxy, nitro, $C_{1-6}$ alkoxy, $C_{1-6}$ alkylcarbonyloxy and halogen atom, or (v) an N-containing heterocyclic ring formed by $R^6$ and $R^7$ in combination with the adjacent nitrogen atom selected from the group consisting of:

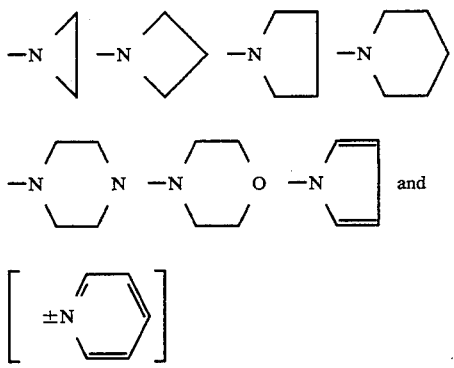

each of which may substituted with one to four substituent(s) selected from the group consisting of (a) a $C_{1-6}$ alkyl group which may be substituted with one to four substituent(s) selected from the group consisting of a hydroxyl, an amino, a mono- or di-$C_{1-6}$ alkylamino, a $C_{1-6}$ alkoxy, a $C_{1-6}$ alkylcarbonyloxy and a halogen, (b) an amino group which may be substituted with one or two substituent(s) selected from the group consisting of a $C_{1-6}$ alkyl, a $C_{1-6}$ acyl, a pyrrolidino, a morpholino, a piperidino and a 1-piperazinyl, (c) a hydroxy, (d) a carboxy, (e) a nitro, (f) a $C_{1-6}$ alkoxy and (g) a halogen; m and n denote a whole number of one to four, respectively, or a pharmaceutically acceptable salt thereof.

2. A compound as claimed in claim 1, wherein $R^1$ stands for a hydrogen atom or a $C_{1-3}$ alkyl group.

3. A compound as claimed in claim 1, wherein $R^2$ and $R^3$ respectively stand for a hydrogen atom or a $C_{1-3}$ alkyl group.

4. A compound as claimed in claim 1, wherein $R^4$ and $R^5$ respectively stand for (i) a hydrogen atom or (ii) a $C_{1-3}$ alkyl group which may be substituted with one to four substituents selected from the group consisting of hydroxy, amino, carboxy, nitro, mono- or di-$C_{1-6}$ alkyl amino, $C_{1-6}$ alkoxy, $C_{1-6}$ alkylcarbonyloxy and halogen, or (iii), taken together with the adjacent carbon atom, form a group of the formula:

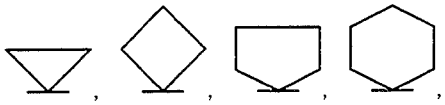

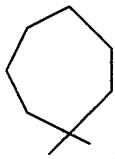

5. A compound as claimed in claim 1, wherein $R^2$, $R^3$, $R^4$ and $R^5$ respectively stand for a hydrogen atom or a $C_{1-3}$ alkyl group.

6. A compound as claimed in claim 1, wherein $R^2$ and $R^3$ respectively stand for a $C_{1-3}$ alkyl group.

7. A compound as claimed in claim 1, wherein $R^4$ and $R^5$ stand for a $C_{1-3}$ alkyl group.

8. A compound as claimed in claim 1, wherein $R^4$ and $R^5$, taken together, with the adjacent carbon atom, form a group of the formula:

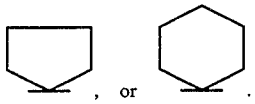

9. A compound as claimed in claim 1, wherein A is an amino group which may be substituted with one or two $C_{1-3}$ alkyl groups.

10. A compound as claimed in claim 1, wherein A is an amino group.

11. A compound as claimed in claim 1, wherein $R^1$ is a hydrogen atom.

12. A compound as claimed in claim 1, wherein $R^2$ and $R^3$ are a hydrogen atom.

13. A compound as claimed in claim 1, wherein $R^4$ and $R^5$ are a hydrogen atom.

14. A compound as claimed in claim 1, wherein m and n respectively stand for 1 or 2.

15. A compound as claimed in claim 1, wherein m and n both are 2.

16. A compound as claimed in claim 1, wherein X is a methine group (i.e. the group —CH=).

17. A compound as claimed in claim 1, wherein X is a nitrogen atom.

18. A compound as claimed in claim 1, wherein x stand for a methine group (i e the group —CH=), $R^1$ stands for a hydrogen atom, $R^2$, $R^3$, $R^4$ and $R^5$ respectively stands for a hydrogen atom or a $C_{1-3}$ alkyl group, A stands for an amino group, and m and n respectively stands for 1, 2 or 3.

19. A compound as claimed in claim 1, wherein X stands for the group —CH=, $R^1$ and $R^2$ both stand for a hydrogen atom, $R^3$, $R^4$ and $R^5$ respectively stand for a $C_{1-3}$ alkyl group, A stands for an amino group, and m and n both are 2.

20. A compound as claimed in claim 1, wherein X stands for a nitrogen atom, $R^1$ is a hydrogen atom, $R^2$, $R^3$, $R^4$ and $R^5$ respectively stand for a hydrogen atom or a $C_{1-3}$ alkyl group, A stands for an amino group, and m and n both are 2.

21. A compound as claimed in claim 1, wherein the salt is a hydrochloride.

22. A compound as claimed in claim 1, which is 6-(3,3-dimethyl-5-sulfamoyl-1-pentyl)imidazo[1,2-b]pyridazi ne.

23. A compound as claimed in claim 1, which is 6-(3,3-dimethyl-5-sulfamoyl-1-pentyl)-7-methylimidazo[1,2 -6]pyridazine.

24. A compound as claimed in claims 1, which is 6-(3,3-dimethyl-5-sulfamoyl-1-pentyl)imidazo[1,2-b]pyrida zine hydrochloride.

25. A compound as claimed in claim 1, which is 6-(3,3-dimethyl-5-sulfamoyl-1-pentyl)-7-methylimidazo[1,2 -b]pyridazine hydrochloride.

26. An antiasthmatic or bronchoconstruction inhibitor composition which comprises an effective amount of a compound as claimed in claim 1, and a physiologically acceptable carrier.

27. A composition as claimed in claim 26 which comprises an effective amount of a compound wherein X stands for the group —CH=, $R^1$ and $R^2$ both stand for a hydrogen atom, $R^3$, $R^4$ and $R^5$ respectively stand for a $C_{1-3}$ alkyl group, A stands for an amino group, and m and n both are 2, or a physiologically acceptable salt thereof.

28. A method for treating asthma in mammals which comprises administrating to a subject suffering therefrom an effective amount of a compound as claimed in claim 1 with a physiologically acceptable carrier.

29. A method for suppressing bronchismus or bronchoconstriction in mammals which comprises administrating to a subject suffering therefrom an effective amount of a compound as claimed in claim 1 with a physiologically acceptable carrier.

* * * * *